United States Patent [19]

Alferness

[11] Patent Number: 5,531,768

[45] Date of Patent: Jul. 2, 1996

[54] IMPLANTABLE ATRIAL DEFIBRILLATOR HAVING ISCHEMIA COORDINATED INTERVENTION THERAPY AND METHOD

[75] Inventor: Clifton A. Alferness, Redmond, Wash.

[73] Assignee: InControl, Inc., Redmond, Wash.

[21] Appl. No.: 391,156

[22] Filed: Feb. 21, 1995

[51] Int. Cl.[6] .................................................. A61N 1/39
[52] U.S. Cl. ............................................................. 607/6
[58] Field of Search ................................ 607/4, 5, 6, 14; 128/696, 702, 705

[56] References Cited

U.S. PATENT DOCUMENTS 5,199,428  4/1993  Obel et al. ............................... 128/703

OTHER PUBLICATIONS

*Ventricular Fibrillation Induced by Low–Energy Shocks from Programmable Implantable Cardioverter–Defibrillators in Patients with Coronary Artery Disease*, Lauer et al., Am. J. Cardiology, V. 73, Mar. 15, 1994, pp. 559–563.

*Primary Examiner*—William E. Kamm
*Assistant Examiner*—Scott M. Getzow
*Attorney, Agent, or Firm*—Richard O. Gray, Jr.

[57] ABSTRACT

An atrial defibrillator coordinates atrial cardioversion with ischemia detection. The defibrillator includes a plurality of sense amplifiers for sensing electrical activity of a heart. An ischemia detector is responsive to the sensed electrical activity of the heart for detecting ischemia of the heart. An atrial fibrillation detector is responsive to the sensed electrical activity of the heart for determining if the atria are in need of cardioversion, and a cardiovertor applies cardioverting electrical energy to the atria of the heart if the atria of the heart are in need of cardioversion and if the ischemia detector fails to detect ischemia of the heart.

33 Claims, 2 Drawing Sheets

IMPLANTABLE ATRIAL DEFIBRILLATOR HAVING ISCHEMIA COORDINATED INTERVENTION THERAPY AND METHOD

BACKGROUND OF THE INVENTION

The present invention generally relates to an automatic implantable atrial defibrillator for delivering cardioverting electrical energy to the atria of a human heart when the atria are in need of cardioversion. The present invention is more particularly directed to such an atrial defibrillator which detects for ischemia of the heart before therapy intervention. If ischemia is detected, a normal therapy intervention process is altered, as by withholding application of cardioverting electrical energy until the ischemia is no longer detected.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience reduced cardiac output and an increased irregular heart rate resulting in palpitations of the heart and even dizziness or loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. One such implantable atrial defibrillator is described in U.S. Pat. No. 5,282,837, which issued on Apr. 12, 1991, in the names of John M. Adams and Clifton A. Alferness, for ATRIAL DEFIBRILLATOR AND METHOD, and which is assigned to the assignee of the present invention and incorporated herein by reference. The defibrillator there described includes an atrial fibrillation detector for detecting atrial fibrillation, and a cardiovertor for cardioverting the heart.

Patients who suffer from atrial fibrillation may also suffer from myocardial ischemia. Myocardial ischemia is a condition wherein there is insufficient blood supply to the myocardium (muscles of the heart) to meet the demand of the myocardium for blood. The ultimate result of persistent ischemia is a necrosis or death of a portion of cardiac muscle tissue, known as a myocardial infarct. Such an occurrence is commonly known as a heart attack.

Insufficient blood supply to the myocardium is generally due to an obstruction or thrombus in an artery which supplies blood to the myocardium. Another cause can be atrial fibrillation, wherein the increased heart rate associated with atrial fibrillation increases the work, and hence the blood demand of the myocardium, while the atrial fibrillation at the same time reduces the blood supply.

Myocardial ischemia is usually detected by submitting the patient to a stress test which increases the cardiac demand of the myocardium. During and after the stress test, twelve lead ECG monitoring is utilized to determine if the heart is receiving an adequate supply of blood.

Ischemia, and the myocardial infarcts that it causes, are known to render the heart unstable and more susceptible or vulnerable to various forms of life threatening arrhythmias. As a result, the present invention contemplates avoiding disturbing the heart during those times in which the heart is experiencing an episode of ischemia. More particularly, and in accordance with a preferred embodiment of the present invention, an implantable atrial defibrillator provides such avoidance by withholding application of cardioverting energy to the atria, even though the atria may require cardioversion, until after the ischemic episode has terminated. In accomplishing this end, before the cardioverting energy is applied, an ischemia detector performs an analysis for possible ischemia. The cardioverting energy is not applied until the ischemia detector fails to detect ischemia of the heart. As a result, the atrial defibrillator not only provides cardioversion of the atria when required, but further provides detection of ischemia when such a condition would otherwise have been permitted to persist unnoticed.

SUMMARY OF THE INVENTION

The present invention provides an atrial defibrillator including sensing means for sensing electrical activity of a heart, an ischemia detector responsive to the sensed electrical activity of the heart for detecting ischemia of the heart, and an atrial fibrillation detector responsive to the sensed electrical activity of the heart for determining if the atria are in need of cardioversion. The defibrillator further includes cardioverting means for applying cardioverting electrical energy to the atria of the heart if the atria of the heart are in need of cardioversion and if the ischemia detector fails to detect ischemia of the heart.

The present invention further provides a method of providing therapy to the atria of a heart. The method includes sensing activity of the heart, analyzing the sensed activity to detect for ischemia of the heart, and determining from the sensed activity if the atria are in need of cardioversion. The method includes the further steps of providing cardioverting therapy to the atria if the atria are in need of cardioversion and if ischemia of the heart is not detected, and withholding therapy to the atria if ischemia of the heart is detected.

The present invention still further provides a method of detecting ischemia of a human heart. The method includes the steps of implanting a first electrode within the heart, implanting a second electrode within the heart, sensing electrical activity of the heart between the first and second electrodes to generate an electrogram signal, analyzing the electrogram signal to generate analysis data and applying an ischemia detection criteria to the analysis data.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
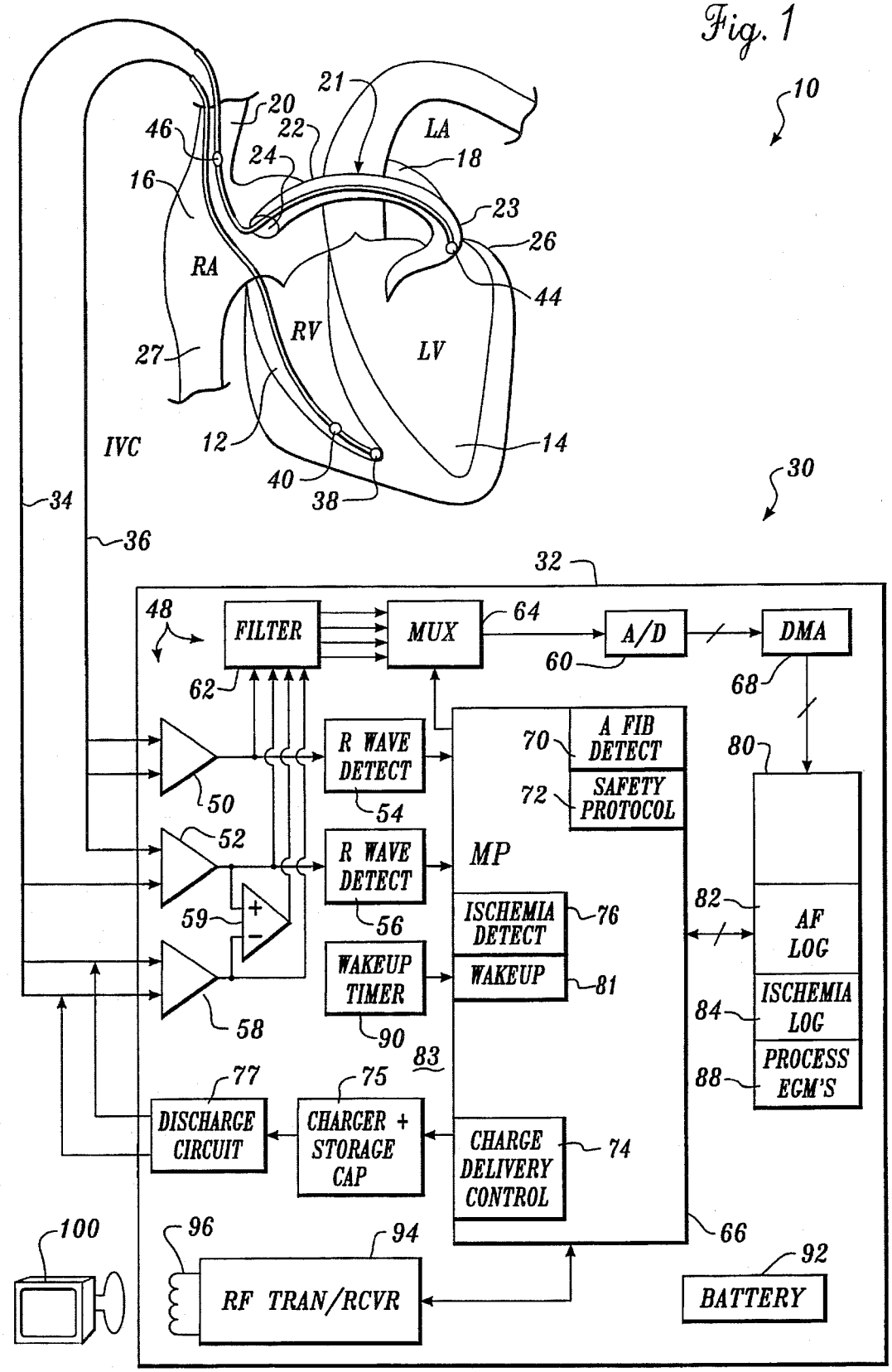
FIG. 1 is a schematic block diagram of a fully implantable atrial defibrillator embodying the present invention.

Referring now to FIG. 1, it illustrates an implantable automatic atrial defibrillator 30 embodying the present invention.

The atrial defibrillator 30 includes an implantable enclosure 32 and an implantable lead system including an intravascular lead 34 and an endocardial lead 36. The endocardial lead 36 has tip and ring electrodes 38 and 40 respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 of lead 34 sense atrial activity of the heart. Electrodes 44 and 46 perform the additional function of applying cardioverting electrical energy across the atria 16 and 18 of the heart.

Electrodes 38 and 40 sense R waves of the heart and may be referred to herein as the first electrode pair. Electrode 44 together with either electrode 38 or electrode 40 also sense R waves of the heart and may be referred to herein as the second electrode pair. The dual sensing of the R waves between the first and second electrode pairs is performed for the purpose of reliably sensing the R waves as fully described in U.S. Pat. No. 5,348,021, which issued on Sep. 20, 1994, for "APPARATUS AND METHOD FOR RELIABLY DETECTING A DEPOLARIZATION ACTIVATION WAVE OF THE HEART AND ATRIAL DEFIBRILLATOR UTILIZING SAME", which is assigned to the assigned of the present invention and incorporated herein by reference.

The implantable enclosure 32 includes a microprocessor 66 and a memory 80. The microprocessor controls the overall function of the atrial defibrillator 30 under software controlled by operating instructions stored in a memory 80. The memory 80 includes a process memory portion 88 for storing electrogram data samples to be processed by the microprocessor 66, an atrial fibrillation log portion 82 for storing atrial fibrillation episode occurrence data, such as electrograms and time and date of detection, and an ischemia log portion 84 for storing similar data relating to the detection of ischemia.

Within the enclosure 32, the atrial defibrillator 30 further includes a data acquisition means 48. The data acquisition means include sense amplifiers 50, 52, and 58, subtractor 59, filter 62, multiplexer 64, analog-to-digital converter 60, direct memory access controller 68, and memory 80.

Sense amplifier 50 is coupled to electrodes 38 and 40 of lead 36 and sense amplifier 52 is coupled to electrode 44 of lead 34 and to either electrode 38 or electrode 40 of lead 36. The sense amplifiers 50 and 52 amplify the first and second electrogram signals provided by the first and second pairs of electrodes respectively to provide R wave detectors 54 and 56 respectively with first and second amplified electrogram signals.

The first electrogram signal is representative of the electrical activity of the right ventricle of the heart. The second electrogram signal is representative of the electrical activity of the heart as sensed between the coronary sinus 22 or great vein 23 and the right ventricle. The second electrogram may therefore be referred to as a right ventricle to coronary sinus electrogram signal.

The R wave detectors 54 and 56 each include a threshold circuit which isolates the R waves from the first and second amplified electrograms provided by sense amplifiers 50 and 52. The outputs of the R wave detectors 54 and 56 are coupled to the microprocessor for conveying the isolated R waves to the microprocessor 66.

Sense amplifier 58 is coupled to electrodes 44 and 46 of lead 34. The sense amplifier 58 amplifies the third electrogram signal provided by electrodes 44 and 46 to provide an amplified third electrogram signal. The third electrogram provided by sense amplifier 58 predominantly represents atrial activity of the heart 10 and may be referred to as a right atrium to coronary sinus electrogram signal.

The subtractor 59 receives the second electrogram signal from the sense amplifier 52, and the third electrogram signal from the sense amplifier 58. As the input polarities indicate, the subtractor 59 subtracts the third electrogram signal (right atrium to coronary sinus) from the second electrogram signal (right ventricle to coronary sinus). This produces a fourth electrogram signal representing the electrical activity of the heart between the right atrium and right ventricle.

The outputs of the sense amplifiers 50, 52 and 58, and the subtractor 59 are coupled to an analog-to-digital converter 60 through the filter 62 and the multiplexer 64. The analog-to-digital converter 60 digitizes the first, second, third and fourth electrograms to generate electrogram digital data samples. The electrogram samples are conveyed to the direct memory access 68 which then stores the electrogram samples in memory portion 88 of memory 80.

When the atrial defibrillator 30 is to determine if the heart 10 is to be cardioverted, a wakeup timer 90 causes a wakeup 81 to enable eight seconds of electrogram digital data to be acquired from amplifiers 50, 52 and 58, and subtractor 59, and to be stored in memory portion 88. The microprocessor then accesses that data, representing the first and third electrograms, when implementing the atrial fibrillation detector 70 to determine if the atria are in fibrillation. The atrial fibrillation detector may be implemented as disclosed in copending U.S. application Ser. No. 08/233,251, filed Apr. 26, 1994, in the names of Harley White and Joseph Bocek, for "SELECTIVE CARDIAC ACTIVITY ANALYSIS ATRIAL FIBRILLATION DETECTION SYSTEM AND METHOD AND ATRIAL DEFIBRILLATOR UTILIZING SAME", and/or copending U.S. application Ser. No. 08/278,055, filed Jul. 20, 1994, in the names Jaeho Kim and Harley White, for "SYSTEM AND METHOD FOR REDUCING FALSE POSITIVES IN ATRIAL FIBRILLATION DETECTION", which applications are assigned to the assignee of the present invention and incorporated herein by reference.

For detecting ischemia, the use of the second and fourth electrograms is preferred. The reason for this is that the second electrogram signal is representative of the electrical activity of the heart between electrode 44 and either electrode 38 and 40. Similarly, the fourth electrogram signal is representative of the electrical activity of the heart between electrode 46 and either electrode 38 and 40. Both electrograms are therefore derived from widely spaced electrodes with the vector therebetween extending across a major portion of the myocardium of the left ventricle and the right ventricle. These muscles are of prominent importance in the proper physiologic operation of the heart. Since ischemia is a condition which affects heart muscle, and if it is present, it will be manifested the most in the left or right ventricular myocardium.

As described in U.S. Pat. No. 5,135,004, which is incorporated herein by reference, one manifestation of ischemia is in deviations of the ST segments in the generated electrograms. Hence, the ischemia detector 76 may process the second and fourth electrogram data in a manner as described in U.S. Pat. No. 5,135,004 to generate ST segment deviations. The ST segment deviations may then be averaged and the average compared to a predetermined ischemia standard of, for example, 1.5 millivolts. If the average exceeds the standard, ischemia will be considered to be detected. An average less than the standard will be considered as a failure to detect ischemia.

Other forms of ischemia analysis may also be used to detect ischemia without departing from the present invention. For example, the morphology of the electrogram may be analyzed. One morphologic characteristic which may be used is the width of the T waves. The width or time duration of the T waves may be generated and averaged. A T wave detection average greater than a predetermined ischemia standard of, for example, 120 milliseconds, may be considered as a successful detection of ischemia. Conversely, an average T wave duration of less than the standard may be considered a failure to detect ischemia.

Another method of generating the fourth electrogram is to numerically subtract the stored third electrogram data from the stored second electrogram data. This would obviate the need for the subtractor 59 and the storage of data from the fourth channel.

In accordance with the present invention, if the atria are in need of cardioversion, but ischemia has also been detected, the therapy intervention sequence which would otherwise be used to cardiovert the heart is altered. More specifically, the sequence alteration preferably takes the form of withholding the application of cardioverting electrical energy to the atria until the ischemia detector fails to detect ischemia while the atria are in need of cardioversion. In this way, the atrial defibrillator avoids disturbing the heart when it is more vulnerable to a ventricular arrhythmia.

If cardioversion is required and permitted, the microprocessor 66, under software control pursuant to operating instructions obtained from the memory 80, implements the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor, through the charge and delivery control 74, terminates the charging.

After the charging of the storage capacitor is completed, and if the atria are to be cardioverted, the microprocessor implements a safety protocol 72. This confirms that R waves are being reliably sensed and detects for a cardiac interval which is longer than a preselected minimum time interval, as fully described in U.S. Pat. No. 5,207,219, which issued on May 4, 1993, for "ATRIAL DEFIBRILLATOR AND METHOD FOR PROVIDING INTERVAL TIMING PRIOR TO CARDIOVERSION", which is assigned to the assignee of the present invention and incorporated herein by reference.

Upon the successful completion of the safety protocol, the charge and delivery control 74 causes a discharge circuit 77, which is coupled to the storage capacitor of circuit 75, to discharge a portion of the energy stored in the storage capacitor. The discharged energy is applied to electrodes 44 and 46 of the intravascular lead 34 for applying the cardioverting electrical energy to the atria 16 and 18 of the heart 10.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the memory 80.

The entire cardioversion sequence, from original detection of an atrial fibrillation episode through successful cardioversion, is initiated at spaced apart predetermined times under the control of an activating means 83, including the wakeup timer 90 and the wakeup 81 of microprocessor 66. The predetermined time is preferably a programmable parameter of the atrial defibrillator 30 and provides wakeup of the atrial defibrillator 30 at spaced apart times for the detection and cardioversion of atrial fibrillation. As a result, the wakeup timer 90 may be reset after the detection of ischemia, after the completion of therapy, and after the completion of each atrial fibrillation detection which does not require intervention. As an example, atrial fibrillation detection may be initiated once every minute to once every twenty minutes.

Figure 2:
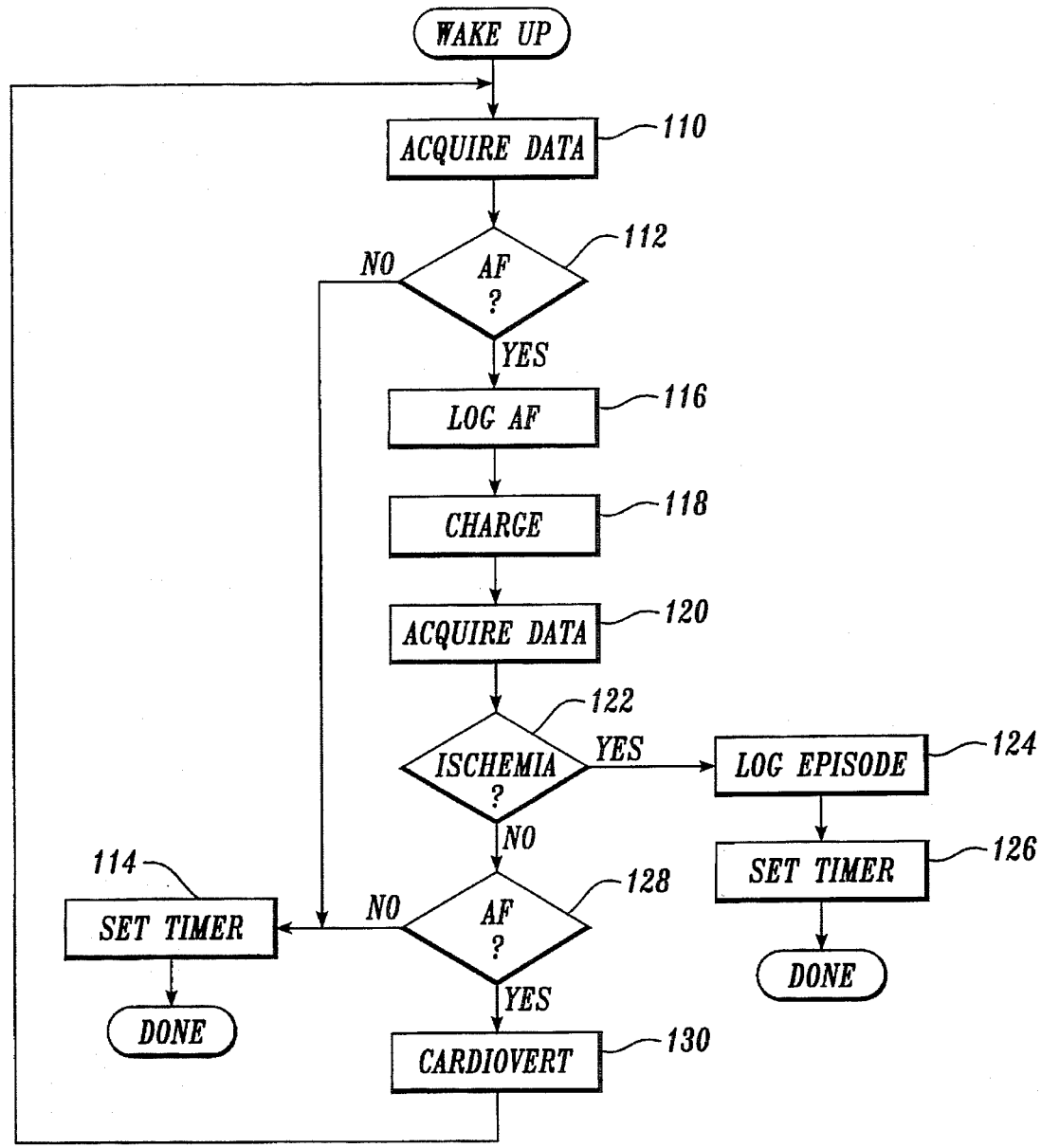
FIG. 2 is a flow diagram illustrating the manner in which the defibrillator of FIG. 1 may be implemented in accordance with a preferred embodiment of the present invention.

The manner in which the atrial defibrillator 30 detects an atrial fibrillation episode and cardioverts the atrial fibrillation episode in accordance with a preferred embodiment of the present invention will now be described with reference to FIG. 2.

The microprocessor 66 and hence the atrial fibrillation detector 70 are normally in a deactivated state along with sense amplifiers 50, 52, and 58, R wave detectors 54 and 56, multiplexer 64, analog-to-digital converter 60, direct memory access 68, and memory 80. As previously mentioned, when the wakeup timer 90 times a predetermined time interval, it causes the wakeup 81 of the atrial defibrillator 30 to initiate detection of a possible atrial fibrillation episode. When the atrial defibrillator 30 is to detect for an atrial fibrillation episode, the wakeup timer 90 causes the wakeup 81 of the microprocessor 66 to first activate the sense amplifiers 50, 52, and 58, the analog-to-digital converter 60, the direct memory access 68 and the memory 80 to initiate an eight second data acquisition period in step 110. During this acquisition period, the microprocessor 66 causes the multiplexer 64 to alternately couple the outputs of sense amplifiers 50, 52 and 58, and subtractor 59, to the analog-to-digital converter 60 to permit the storing of digital samples of the first, second, third and fourth electrograms in the process memory portion 88 of the memory 80.

When the eight second acquisition is completed, the microprocessor 66 implements the atrial fibrillation detector 70, in accordance with step 112, by processing the first and third electrogram data stored in the process memory portion 88 to detect for atrial fibrillation in accordance with an atrial fibrillation detection algorithm. If atrial fibrillation is not detected, the process returns with the wakeup 81 of the microprocessor deactivating the data acquisition means 48, resetting the wakeup timer 90, and then deactivating the microprocessor 66 in step 114. The wakeup timer 90 then proceeds to time its predetermined time interval to once again activate the wakeup 81 of microprocessor 66 at the next time in which a possible atrial fibrillation episode is to be detected.

If atrial fibrillation is detected in step 112, the microprocessor logs the detection of an atrial fibrillation episode in step 116. This may be performed by storing in memory portion 82 the date and time of the atrial fibrillation detection, and the electrogram data of the third electrogram.

If atrial fibrillation is detected in step 112 by the atrial fibrillation detector 70, the charge delivery control 74 causes the charge and storage capacitor circuit 75 to charge the storage capacitor to a preselected peak voltage in step 118. When the capacitor is charged, another data acquisition is performed in step 120, as previously described. The ischemia detector 76 then, in step 122, determines if the heart is currently suffering an ischemic episode. The ischemia detector preferably applies ischemia criteria to ischemia data generated by the microprocessor from the second and fourth electrogram data, as previously described. If the ischemia detector detects ischemia, the intervention sequence is altered by logging the detection of the ischemia episode in step 124 by storing the data and time of detection and the second and fourth electrogram data in memory portion 84. Then, in step 126, the wakeup timer 90 is reset and the process returns.

If ischemia is not detected in step 122, the atrial fibrillation detector 70, in step 128, once again determines if the atria 16 and 18 of the heart 10 are still in fibrillation. If the atrial fibrillation detector 70 determines that the atria are not still in fibrillation, the process is completed and the wakeup timer 90 is reset by performing step 114, and the process returns. The wakeup timer 90 then proceeds to time its predetermined time interval.

However, if the atria are still in fibrillation, the microprocessor 66 then applies cardioverting electrical energy to the atria in step 130 by first implementing the safety protocol 72, as previously described. When the safety protocol is completed, the charge delivery control 74 causes the discharge circuit 77 to discharge a portion of the energy stored in the storage capacitor of circuit 75 between electrodes 44 and 46 for cardioverting the atria of the heart.

Following the delivery of the cardioverting electrical energy to the atria, in step 130, the foregoing process is repeated, beginning with another eight second data acquisition being performed in accordance with step 110. Hence, the process completes and returns if atrial fibrillation is not originally detected, if the atria are in atrial fibrillation and the heart is suffering from ischemia, or if the atria have been successfully cardioverted. When the process returns, the wakeup timer 90 is reset to time its predetermined time interval for initiating the detection of a possible atrial fibrillation episode at the next predetermined time.

As a result of the foregoing, the atrial defibrillator of the present invention alters its therapy intervention if therapy is required, but ischemia has also been detected. By withholding cardioversion under these conditions, the heart is not disturbed when it is potentially vulnerable to a ventricular arrhythmia. Also, as a result, valuable ischemia data may be made available to the physician for use in future treatment of the patient.

While a particular embodiment of the present invention has been shown and described, modifications may be made. For example, the present invention may also be employed to advantage in defibrillators which continuously monitor heart activity for possible fibrillation. Such a defibrillator is described, for example, in U.S. Pat. No. 5,282,837, which issued on Feb. 1, 1994, for "ATRIAL DEFIBRILLATOR AND METHOD", which patent is also assigned to the assignee of the present invention and incorporated herein by reference. It is therefore intended in the appended claims to cover all such changes and modifications which fall within the true spirit and scope of the invention.

What is claimed is:

1. An atrial defibrillator comprising:
   sensing means for sensing electrical activity of a heart;
   an ischemia detector responsive to the sensed electrical activity of the heart for detecting ischemia of the heart;
   an atrial fibrillation detector responsive to the sensed electrical activity of the heart for determining if the atria are in need of cardioversion; and
   cardioverting means for applying cardioverting electrical energy to the atria of the heart if the atria of the heart are in need of cardioversion and if the ischemia detector fails to detect ischemia of the heart.

2. An atrial defibrillator as defined in claim 1 further including ischemia data generating means for generating ischemia data responsive to the sensed electrical activity of the heart and memory means for storing the ischemia data when the ischemia detector detects ischemia of the heart.

3. An atrial defibrillator as defined in claim 2 wherein the ischemia data includes ST segment deviation data.

4. An atrial defibrillator as defined in claim 2 wherein the ischemia data includes data representative of T wave morphology of the heart.

5. An atrial defibrillator as defined in claim 2 further including telemetry means for transmitting the stored ischemia data to a nonimplanted external receiver.

6. An atrial defibrillator as defined in claim 1 wherein the atrial fibrillation detector determines if the atria are in need of cardioversion if the ischemia detector first fails to detect ischemia of the heart.

7. An atrial defibrillator as defined in claim 1 further including heart activity data generating means for generating heart activity data responsive to the sensed electrical activity of the heart and memory means for storing said heart activity data, said atrial fibrillation detector and said ischemia detector being responsive to the stored heart activity data.

8. An atrial defibrillator as defined in claim 7 wherein the heart activity data includes data representing ST segment amplitudes of the heart.

9. An atrial defibrillator as defined in claim 7 wherein the heart activity data includes data representative of T wave morphology of the heart.

10. An atrial defibrillator as defined in claim 9 wherein the T wave morphology data is representative of T wave width.

11. An atrial defibrillator as defined in claim 1 wherein the sensing means includes first sensing means for sensing electrical activity of the right ventricle of the heart to produce a first electrogram signal.

12. An atrial defibrillator as defined in claim 1 wherein the sensing means includes second sensing means for sensing electrical activity of the heart between the coronary sinus or great vein of the heart and the right ventricle of the heart to produce a second electrogram signal.

13. An atrial defibrillator as defined in claim 12 wherein the sensing means includes a third sensing means for sensing electrical activity of the heart between the right atrium and the coronary sinus or great vein of the heart to produce a third electrogram signal.

14. An atrial defibrillator as defined in claim 13 further including subtracting means for subtracting the third electrogram signal from the second electrogram signal to produce a fourth electrogram signal.

15. An atrial defibrillator as defined in claim 14 wherein the ischemia detector is responsive to the second and fourth electrogram signals for detecting ischemia of the heart.

16. A method of providing therapy to the atria of a heart, said method comprising the steps of:

sensing activity of the heart;

analyzing the sensed activity to detect for ischemia of the heart;

determining from the sensed activity if the atria are in need of cardioversion;

providing cardioverting therapy to the atria if the atria are in need of cardioversion and if ischemia of the heart is not detected; and withholding therapy to the atria if ischemia of the heart is detected.

17. A method as defined in claim 16 further including the step of generating ischemia data responsive to the sensed electrical activity of the heart and storing the ischemia data in memory when ischemia of the heart is detected.

18. A method as defined in claim 17 wherein the ischemia data includes ST segment deviation data.

19. A method as defined in claim 17 wherein the ischemia data includes data representative of T wave morphology of the heart.

20. A method as defined in claim 17 including the further step of transmitting the stored ischemia data to a nonimplanted external receiver.

21. A method as defined in claim 16 wherein the step of determining if the atria are in need of cardioversion is performed only if ischemia of the heart is not detected.

22. A method as defined in claim 16 further including the steps of generating heart activity data responsive to the sensed electrical activity of the heart, and storing the heart activity data, wherein said analyzing and determining steps being performed with the stored heart activity data.

23. A method as defined in claim 22 wherein the heart activity data includes data representing ST segment amplitudes of the heart.

24. A method as defined in claim 22 wherein the heart activity data includes data representative of T wave morphology of the heart.

25. A method as defined in claim 24 wherein the T wave morphology data is representative of T wave width.

26. A method as defined in claim 16 wherein the sensing step includes sensing electrical activity of the right ventricle of the heart.

27. A method as defined in claim 16 wherein the sensing step includes sensing electrical activity of the heart between the coronary sinus or great vein of the heart and the right ventricle of the heart.

28. A method as defined in claim 16 wherein the sensing step includes establishing electrical contact between the right atrium of the heart and a right atrial electrode, establishing electrical contact between the right ventricle of the heart and a right ventricular electrode, and generating an electrogram signal representing the electrical activity of the heart between the right atrial and the right ventricular electrodes.

29. A method as defined in claim 28 wherein the sensing step includes sensing electrical activity of the heart between the right atrium and the coronary sinus or grat vein of the heart to produce a right atrium to coronary sinus electrogram signal.

30. A method as defined in claim 29 wherein the sensing step includes sensing electrical activity of the heart between the coronary sinus or great vein of the heart and the right ventricle of the heart to produce a right ventricle to coronary sinus electrogram signal.

31. A method as defined in claim 30 wherein the sensing step includes subtracting the right atrium to coronary sinus electrogram signal from the right ventricle to coronary sinus electrogram signal to produce the electrogram signal representing the electrical activity of the heart between the right atrial and right ventricular electrode.

32. An atrial defibrillator comprising:

sensing means for sensing electrical activity of a heart;

an ischemia detector responsive to the sensed electrical activity of the heart for detecting ischemia of the heart;

an atrial fibrillation detector responsive to the sensed electrical activity of the heart for determining if the atria are in need of cardioversion; and therapy means for providing a predetermined therapy to the atria of the heart if the atria of the heart are in need of cardioversion and if the ischemia detector fails to detect ischemia of the heart and for altering said predetermined therapy if the atria are in need of cardioversion and the ischemia detector detects ischemia of the heart.

33. A method of providing therapy to the atria of a heart, said method comprising the steps of:

sensing activity of the heart;

analyzing the sensed activity to detect for ischemia of the heart;

determining from the sensed activity if the atria are in need of cardioversion;

providing a predetermined therapy to the atria if the atria are in need of cardioversion and if ischemia of the heart is not detected; and altering said predetermined therapy if ischemia of the heart is detected.

* * * * *